United States Patent [19]

Kumata et al.

[11] Patent Number: 5,457,255

[45] Date of Patent: Oct. 10, 1995

[54] CATALYSTS FOR HYDROGENOLYTIC DEALKYLATION AND USE THEREOF

[75] Inventors: Fumio Kumata; Toshihiko Masuda; Iwao Ueda, all of Kanagawa, Japan

[73] Assignee: Mitsubishi Oil Co., Ltd., Tokyo, Japan

[21] Appl. No.: 248,530

[22] Filed: May 24, 1994

Related U.S. Application Data

[63] Continuation of Ser. No. 774,944, Oct. 11, 1991, abandoned.

[30] Foreign Application Priority Data

Oct. 12, 1990 [JP] Japan .................................. 2-272301

[51] Int. Cl.$^6$ .................................. C07C 4/12; C07C 4/18
[52] U.S. Cl. ........................ 585/488; 585/483; 585/486
[58] Field of Search ................................ 585/483, 484, 585/485, 486, 488, 489

[56] References Cited

U.S. PATENT DOCUMENTS

| | | | |
|---|---|---|---|
| 3,700,745 | 10/1972 | Kovach et al. | 585/485 |
| 4,320,242 | 3/1982 | Onodera et al. | 585/486 |
| 4,485,185 | 11/1984 | Onodera et al. | 502/77 |
| 4,622,308 | 11/1986 | Koikeda et al. | 502/77 |
| 4,681,747 | 7/1987 | Desmond et al. | 502/77 |
| 5,008,094 | 4/1991 | Keijsper et al. | 502/77 |
| 5,028,573 | 7/1991 | Brown et al. | 502/71 |

FOREIGN PATENT DOCUMENTS

| | | | |
|---|---|---|---|
| 136068 | 4/1985 | European Pat. Off. | 502/77 |
| 2351930 | 5/1976 | France . | |
| 53-41658 | 6/1978 | Japan . | |
| 58-210851 | 12/1983 | Japan . | |

*Primary Examiner*—P. Achutamurthy
*Attorney, Agent, or Firm*—Sughrue, Mion, Zinn, Macpeak & Seas

[57] ABSTRACT

A catalyst for hydrogenolytic dealkylation comprising rhodium on a crystalline metallo-silicate carrier and a process for hydrogenolytically dealkylating a hydrocarbon mixture mainly comprising alkyl aromatic hydrocarbons in the presence of such a catalyst are disclosed. The catalyst exhibits catalytic activity at low temperatures and high reaction selectivity and has a prolonged duration.

5 Claims, No Drawings

CATALYSTS FOR HYDROGENOLYTIC DEALKYLATION AND USE THEREOF

CROSS REFERENCE TO RELATED APPLICATIONS

This is a continuation of application Ser. No. 07/774,944, filed Oct. 11, 1991, now abandoned

FIELD OF THE INVENTION

This invention relates to a catalyst for hydrogenolytic dealkylation of alkyl aromatic hydrocarbons and usage thereof. More particularly, it relates to a catalyst to be used in processes for catalytically dealkylating hydrocarbons containing an alkyl aromatic hydrocarbon having from 7 to 10 carbon atoms in the presence of hydrogen and to a process for using the same.

BACKGROUND OF THE INVENTION

Industrially practical processes of catalytic hydrogenolytic dealkylation of aromatic hydrocarbons typically include processes in which a reaction is conducted at a high temperature between 600° C. and 650° C. in the presence of a chromia-alumina catalyst as disclosed, e.g., in U.S. Pat. No. 2,951,886. These processes primarily aim at demethylation of toluene, uses of which, except for gasoline and a solvent, are restricted, to produce benzene useful as a raw material of nylon synthesis.

While no noteworthy improvement has ever been added to these processes, Neftekhimiya, Vol. 15, No. 1, p. 95 (1975) reports that demethylation of toluene for production of benzene can be carried out at a temperature lower than the conventionally employed range, i.e., between 400° C. and 500° C., by using a catalyst comprising a novel metal of the Group VIII, e.g., ruthenium, rhodium, palladium, osmium, iridium, and platinum, supported on an alumina carrier.

However, since the novel metal-on-carrier catalysts need further improvements in activity, durability, reaction selectivity, and the like, many proposals have been made, for example, a combined use of two or more novel metals and addition of other transition metal components.

For example, JP-A-58-210851 (the term "JP-A" as used herein means an "unexamined published Japanese patent application") proposes a catalyst having improved low-temperature activity, which is obtained by impregnating rhodium into an alumina carrier followed by calcination in an oxygen atmosphere, and JP-A-58-210851 proposes a catalyst having improved low-temperature activity and prolonged duration, which is obtained by supporting iridium and an alkaline earth metal on an alumina carrier.

These improved catalysts are still unsatisfactory in terms of catalytic activity, duration, and reaction selectivity when applied to heavy aromatic hydrocarbons containing 8 to 10 carbon atoms.

On the other hand, known crystalline methallo-silicate catalysts for reactions of aromatic hydrocarbons include those for disproportionation (JP-A-52-65229), those for isomerization (JP-B-53-41658, the term "JP-B" as used herein means an "examined published Japanese patent application"), and those for alkylation (JP-B-56-44050), and some of them have been put to practical use. A crystalline metallo-silicate catalyst predominantly catalyzing dealkylation of aromatic hydrocarbons is unknown.

The above-mentioned processes conventionally adopted on an industrial scale are associated with serious problems such that (1) the reaction temperature is as high as 600° to 650° C., (2) even starting with any alkyl-substituted aromatic hydrocarbon other than toluene which has been used as a main starting material of dealkylation, e.g., ethylbenzene, dimethylbenzene (xylene), propylbenzene, and methylethylbenzene, the reaction results in production of benzene in a major proportion, with surprising low selectivity to toluene or xylene which is a useful chemical raw material, and (3) reduction in catalytic activity is more noticeable as the starting aromatic hydrocarbon becomes heavier.

While the reaction temperature can be dropped to 500° C. or less by using the above-described novel metal-on-alumina catalyst, the literature affords no working example of starting with heavy aromatic hydrocarbons having 8 to 10 carbon atoms. Moreover, the problems relating to low reaction selectivity and high rate of activity reduction have not yet been settled.

SUMMARY OF THE INVENTION

An object of the present invention is to provide a catalyst with which benzene, toluene, and xylene can be produced from not only toluene but heavy aromatic hydrocarbons having 8 to 10 carbon atoms at low temperatures at which by-production of coke causing reduction of catalytic activity is suppressed.

Another object of the present invention is to provide a process for producing aromatic hydrocarbons by using such a catalyst.

As a result of extensive investigations to accomplish the above objects of the present invention, the inventors have found that a catalyst prepared by supporting rhodium on a crystalline metallo-silicate carrier exhibits catalytic activity in lower temperatures and has high reaction selectivity and prolonged duration.

The present invention relates to a catalyst comprising rhodium supported on a crystalline metallo-silicate carrier.

The present invention also relates to a process for dealkylating a hydrocarbon mixture containing an alkyl-substituted aromatic hydrocarbon, particularly an aromatic hydrocarbon substituted with an alkyl group having 2 or more carbon atoms in the presence of a catalyst comprising rhodium supported on a crystalline metallo-silicate carrier.

In the dealkylation reaction according to the present invention, the alkyl group(s) of the starting aromatic hydrocarbon is/are converted to an alkyl-group having a carbon atom number reduced by one in a successive manner. This means that the hydrogenolysis (hydrocracking) of the alkyl group starts from the carbon atom farthest from the benzene ring.

Aromatic hydrocarbons having from 9 to 10 carbon atoms are mainly produced as by-products in catalytic reforming process for petroleum refining. Their uses are confined to solvents and materials to be mixed with gasoline. The present invention makes it possible to use these heavy aromatic hydrocarbons as starting oils for producing more valuable benzene, toluene and xylene.

DETAILED DESCRIPTION OF THE INVENTION

A carrier of the catalyst according to the present invention is a crystalline metallo-silicate. The terminology "metallo-silicate" as used herein means a crystalline substance showing the same or similar pattern in powder X-ray analysis as that of a pentasil type zeolite exemplified by ZSM-5 and includes crystalline aluminosilicate and crystalline aluminosilicate whose aluminum and/or silicon is partially replaced with other metals.

Metals in crystalline metallo-silicates include the group III elements, e.g., aluminum and gallium; the group IV elements, e.g., germanium; the group V elements, e.g., arsenic and bismuth; the group VI elements, e.g., chromium; the group VII elements, e.g., manganese; the group VIII elements, e.g., iron and cobalt; and lanthanide elements, e.g., lanthanum and cerium. Preferred crystalline metallo-silicates are crystalline aluminoferrosilicate and crystalline aluminolanthanosilicate having iron or lanthanum in place of part of aluminum and/or silicon by isomorphous substitution.

The composition of a reaction product varies depending on the molar ratio of silicon oxide to a metal oxide in the crystalline metallo-silicate. Taking crystalline aluminosilicate for instance, its acidity varies depending on the $SiO_2/Al_2O_3$ molar ratio, and the composition of a reaction product changes accordingly. At a high $SiO_2/Al_2O_3$ molar ratio, the acidic catalyst activity on an account of a carbonium ion mechanism is reduced, which leads to a decomposition reaction resulting in a reduction of light paraffin contents or a disproportionation reaction resulting in a reduction of heavy aromatic contents. Acidity of the carrier also has a slight influence on a dealkylation reaction in such a manner that production of light aromatic hydrocarbons is slightly reduced in using a catalyst having a high $SiO_2/Al_2O_3$ molar ration, i.e., low acidity. Therefore, the optimum $SiO_2/Al_2O_3$ molar ratio should be so determined as to give a desirable yield pattern. In addition, as acidity decreases, by-production of coke is reduced so that the catalyst duration is extended. From these considerations, the $SiO_2/Al_2O_3$ molar ratio preferably ranges from 50 to 1000.

Metals in the crystalline aluminometallo-silicates preferably include iron and lanthanum as stated above. Replacement of part of aluminum and/or silicon of crystalline aluminosilicate with these metals provides a catalyst having particularly high selectivity to demethylation while markedly inhibiting decomposition or disproportionation which is observed in using crystalline aluminosilicate having carried thereon rhodium or a catalyst which is attended by considerable decomposition or disproportionation but exhibits very high activity for demethylation.

Catalytic activity of the aluminometallo-silicate catalysts can be controlled by the degree of replacement with metals. Replacement with iron gives catalysts of high selectivity, and replacement with lanthanum gives catalysts of high activity. A suitable degree of replacement varies depending on the metal. A preferred $SiO_2/Fe_2O_3$ molar ratio is from 25 to 200 at an $SiO_2/Al_2O_3$ molar ratio of from 50 to 1000, and a preferred $SiO_2/La_2O_3$ molar ratio is from 25 to 200 at an $SiO_2/Al_2O_3$ molar ratio of from 50 to 1000.

In the catalyst of the present invention, the active site for dealkylation is rhodium while the role of the carrier portion in dealkylation has not yet been clarified. It is assumed that various effects of the carrier, such as stable dispersion of rhodium, control of diffusion of a starting oil to the active site, a metal-acid binary catalytic function owing to the above-mentioned acidity, and an electron attracting effect owing to a difference from rhodium in electronegativity, are produced in cooperation. Catalytic action is manifested at a trace rhodium content of, e.g., 0.01% by weight. A rhodium content usually ranges from 0.01 to 5% by weight, and preferably from 0.1 to 1.0% by weight.

Crystalline metallo-silicates can be synthesized through various routes including, for example, the process described in Shokubaishi (which means "Catalyst Journal"), Vol. 23, No. 3, p. 232 (1981). While the alkylammonium salt, called a template, used in this particular process is tetrapropylammonium bromide, primary to tertiary amines may also be used to synthesize metallo-silicates of the same crystal structure.

Supporting of rhodium on the carrier can be performed by known impregnation or ion-exchange methods using various water-soluble rhodium salts, e.g., rhodium chloride, rhodium bromide, rhodium iodide, rhodium sulfate, rhodium nitrate, chloropentaaminerhodium chloride, hexaaminerhodium trinitrate, and sodium rhodium chloride.

The rhodium-on-crystalline metallo-silicate catalyst of the present invention is characterized by catalyzing demethylation as a main target while showing a difference in reaction rate according to the state of bonding of a methyl group. More specifically, results of various reactions reveal that the reaction rate decreases in the order of n-propylbenzene, methylethyl benzene, ethylbenzene, trimethylbenzene, dimethylbenzene (xylene), and toluene.

On account of the difference in reaction rate, in the resulting oil are concentrated methyl-substituted compounds, e.g., toluene, xylene, and trimethylbenzene. When, for example, a mixture of aromatic hydrocarbons having 9 carbon atoms is used as a starting oil, n-propylbenzene and methylethylbenzene are preferentially reacted, and trimethylbenzene is hardly reacted. Further, of the produced aromatic hydrocarbons having 8 carbon atoms, ethylbenzene is ready to react whereas dimethylbenzene is hard to react. Eventually, in the resulting oil are concentrated benzene, toluene, xylene, and trimethylbenzene. The resulting oil is easily separated by distillation into benzene for use as, e.g., a raw material for petro-chemical products, e.g., nylon; toluene for use, e.g., as a special solvent; dimethylbenzene for use as, e.g., a raw material for p-xylene; and trimethylbenzene for use as, e.g., a raw material for special petrochemical products.

Conditions of a reaction using the rhodium-on-crystalline metallo-silicate catalyst of the present invention are selected according to the starting oil. In using toluene, the least reactive oil, a suitable temperature range is from 350° to 450° C. In using easily reactive n-propylbenzene or diethylbenzene, a suitable temperature range is from 300° to 400° C. At temperatures lower than the respective lower limit, the reaction does not proceed. At higher temperatures, the reaction is attended by decomposition or formation of coke on the catalyst. While pressure has no noticeable influence on the reaction progress, the reaction rate slightly increases under an elevated pressure. A suitable reaction pressure is in the range of from 5 to 50 kg/cm². Under a lower pressure, catalytic activity tends to decrease at a high rate. Under a higher pressure, an aromatic ring tends to undergo hydrogenolysis (hydrocracking), resulting in a reduction in selectivity. LHSV usually ranges from 0.5 to 10 0 hr⁻¹, and hydrogen is usually used in an amount of from 2 to 5 mols per mol of a starting oil.

The present invention is now illustrated in greater detail by way of Examples, but it should be understood that the present invention is not deemed to be limited thereto. All the percents are by weight unless otherwise indicated.

EXAMPLE 1

Preparation of Crystalline Aluminosilicate

Solution A was prepared by mixing 180 g of deionized water, 6.5 g of aluminum sulfate, 18.6 g of sulfuric acid, and 22.6 g of tetrapropylammonium bromide. Solution B was prepared by mixing 133 g of deionized water and 207 g of water glass (JIS #3). Solution C was prepared by mixing 313 g of deionized water and 78.8 g of sodium chloride.

Each of solutions A and B was put in a dropping funnel and added dropwise to solution C over a period of 30 minutes while vigorously stirring. The resulting mixture was put in a 1 l stainless steel autoclave and allowed to react at 160° C. for 48 hours. After the reaction, the product formed was collected by filtration, washed with deionized water until the washing had a pH of 8, dried at 110° C. for 16 hours, and calcined at 530° C. for 3 hours. Fifty grams of the resulting crystalline aluminosilicate were soaked in 300 ml of a 1N ammonium chloride aqueous solution. After keeping the system at 80° C. for 8 hours, the solution was exchanged. The above operation was repeated 4 times to convert the crystalline aluminosilicate to a proton type. After filtration, the solid was dried at 110° C. for 16 hours and then calcined at 530° C. for 3 hours. Ten grams of the resulting crystalline aluminosilicate of proton type were dipped in 30 ml of deionized water, and 5 ml of an aqueous solution containing 0.1 g of rhodium trichloride was added thereto dropwise with stirring, followed by gently stirring for about 20 hours to thereby allow the rhodium salt to be sufficiently adsorbed on the crystalline aluminosilicate. The mixture was evaporated to dryness, and the residue was dried at 110° C. for 5 hours and calcined at 530° C. for 3 hours. The thus obtained catalyst was designated catalyst A. Catalyst A had a rhodium content of 0.4%.

EXAMPLE 2

Catalysts B, C, and D were prepared in the same manner as in Example 1, except for changing the amount of aluminum sulfate in solution A to 3.2 g, 1.6 g, and 1.1 g, respectively.

The crystalline aluminosilicate in catalysts A, B, C, and D had an $SiO_2/Al_2O_3$ molar ratio of 100, 200, 400, and 600, respectively.

COMPARATIVE EXAMPLE 1

Catalysts a, b, c, and d were prepared in the same manner as in Examples 1 and 2, except that rhodium was not supported on the crystalline aluminosilicate.

EXAMPLE 3 AND COMPARATIVE EXAMPLE 2

Toluene (JIS #1) was reacted in the presence of each of the catalysts prepared in Examples 1 and 2 and Comparative Example 1 under conditions of a temperature of 400° C., a pressure of 8 kg/cm$^2$G, LHSV of 2.0 hr$^{-1}$, and a hydrogen molar ratio of 3. The reaction results are shown in Table 1 below.

TABLE 1

| Composition of Reaction Product (wt %) | Catalyst | | | | | | | |
|---|---|---|---|---|---|---|---|---|
| | A | B | C | D | a | b | c | d |
| Decomposition product | 0.5 | 0.4 | 0.4 | 0.2 | 0.2 | 0.1 | 0.1 | 0.0 |
| Benzene | 3.5 | 3.2 | 2.1 | 1.8 | 3.8 | 2.9 | 2.0 | 1.2 |
| Toluene | 95.4 | 96.0 | 97.2 | 97.7 | 91.4 | 93.3 | 95.2 | 97.0 |
| Xylene | 0.5 | 0.4 | 0.3 | 0.3 | 4.1 | 3.3 | 2.4 | 1.7 |
| $C_{9+}$ Aromatic hydrocarbons | 0.1 | 0.0 | 0.0 | 0.0 | 0.5 | 0.4 | 0.3 | 0.1 |

It can be seen that dealkylation reaction took place at good selectivity in the presence of catalysts A, B, C, and D whereas the reactions in the presence of comparative catalysts a, b, c, and d predominantly produce products resulting from disproportionation, and dealkylation reaction was not a main reaction.

EXAMPLE 4 AND COMPARATIVE EXAMPLE 3

Xylene for isomerization having a low p-xylene content was reacted in the presence of each of the catalysts prepared above under conditions of a temperature of 380° C., a pressure of 8 kg/cm$^2$G, LHSV of 2.0 hr$^{-1}$, and a hydrogen molar ratio of 3. The reaction results are shown in Table 2 below.

TABLE 2

| Composition (wt %) | Starting Oil (wt %) | Catalyst | | | | | | | |
|---|---|---|---|---|---|---|---|---|---|
| | | A | B | C | D | a | b | c | d |
| Decomposition product | 0 | 3.5 | 2.8 | 1.6 | 0.6 | 0.7 | 0.5 | 0.4 | 0.2 |
| Benzene | 0 | 2.9 | 1.7 | 1.3 | 0.4 | 7.8 | 6.3 | 3.5 | 1.8 |
| Toluene | 0 | 11.9 | 9.5 | 6.8 | 3.8 | 8.9 | 7.2 | 3.4 | 2.4 |
| Ethylbenzene | 10.3 | 2.2 | 4.1 | 5.3 | 6.0 | 3.5 | 5.3 | 6.3 | 7.4 |
| p-Xylene | 1.6 | 17.7 | 18.3 | 19.2 | 19.3 | 13.9 | 15.2 | 17.1 | 16.7 |
| m-Xylene | 60.5 | 42.1 | 43.8 | 46.1 | 49.3 | 36.2 | 37.3 | 43.5 | 45.7 |
| o-Xylene | 27.6 | 17.6 | 18.5 | 18.8 | 20.2 | 14.9 | 16.1 | 19.8 | 20.6 |
| Total of xylene | 88.7 | 77.4 | 80.6 | 84.1 | 88.8 | 65.0 | 68.6 | 80.4 | 83.0 |
| $C_{9+}$ Aromatic hydrocarbons | 0 | 2.1 | 1.3 | 0.9 | 0.4 | 14.1 | 6.0 | 6.0 | 5.2 |

It can be seen from Table 2 that in the reactions using catalysts A, B, C, and D ethylbenzene having high dealkylation reactivity decreased and, at the same time, isomerization of xylene also proceeded with a small loss of xylene. To the contrary, in the reactions using catalysts a, b, c, and d, isomerization and disproportionation took place as predominant reactions with a great loss of xylene.

EXAMPLE 5 AND COMPARATIVE EXAMPLE 4

An aromatic hydrocarbon mixture having 9 or 10 carbon atoms was reacted in the presence of catalyst B or b under the same conditions as in Example 4. The reaction results are shown in Tables 3 and 4 below.

TABLE 3

| Composition | Starting Oil | Reaction Products ($C_{9+}$ Aromatic) (wt %) | |
|---|---|---|---|
| | | B | b |
| Decomposition product | | 6.6 | 1.5 |
| Benzene | | 2.7 | 1.2 |
| Toluene | | 8.7 | 3.1 |
| Xylene | | 20.9 | 8.5 |
| Methylethylbenzene | 38.0 | 12.6 | 26.2 |
| Trimethylbenzene | 54.1 | 46.8 | 41.6 |
| Other $C_9$ aromatic hydrocarbons | | 0.6 | 5.1 |
| Other $C_{9+}$ aromatic hydrocarbons | 7.9 | | |
| $C_{10+}$ Aromatic hydrocarbons | | 1.1 | 12.8 |

TABLE 4

| Composition | Starting Oil | Reaction Products ($C_{10+}$ Aromatic) (wt %) | |
|---|---|---|---|
| | | B | b |
| Decomposition product | | 8.4 | 0.9 |
| Benzene | | 1.7 | 0.4 |
| Toluene | | 5.0 | 1.3 |
| Xylene | | 14.8 | 3.6 |
| $C_{9+}$ Aromatic hydrocarbons | | 10.0 | 7.2 |
| Diethylbenzene | 28.6 | 9.5 | 23.1 |
| Dimethylethylbenzene | 22.4 | 11.7 | 17.2 |
| Tetramethylbenzene | 36.5 | 35.2 | 29.9 |
| Other $C_{10}$ aromatic hydrocarbons | | 2.3 | 8.2 |
| Other $C_{10+}$ aromatic hydrocarbons | 12.5 | | |
| $C_{11+}$ Aromatic hydrocarbons | | 1.4 | 9.3 |

As can be seen from Tables 3 and 4, the reaction preferentially started from the ethyl group in the presence of the catalyst according to the present invention, whereas disproportionation reaction predominantly took place in the presence of the comparative catalyst.

EXAMPLE 6

Catalyst E was prepared in the same manner as in Example 1, except for changing the amount of aluminum sulfate in solution A to 1.1 g and further adding 5.4 g of iron chloride to solution A. Catalyst E had an $SiO_2/Al_2O_3$ molar ratio of 600, an $SiO_2/Fe_2O_3$ molar ratio of 100, and a rhodium content of 0.4%.

COMPARATIVE EXAMPLE 5

Catalyst e was prepared in the same manner as in Example 6, except that rhodium was not supported on the carrier.

EXAMPLE 7

Catalyst F was prepared in the same manner as in Example 6, except for replacing iron chloride with 7.4 g of lanthanum chloride. Catalyst F had an $SiO_2/Al_2O_3$ molar ratio of 600, an $SiO_2/La_2O_3$ molar ratio of 100, and a rhodium content of 0.4%.

COMPARATIVE EXAMPLE 6

Catalyst f was prepared in the same manner as in Example 7, except that rhodium was not supported on the carrier.

EXAMPLE 8 AND COMPARATIVE EXAMPLE 7

Toluene or xylene for isomerization was reacted in the presence of catalyst E, F, e, or f under the same conditions as in Example 3 for toluene or Example 4 for xylene for isomerization. The reaction results are shown in Table 5 below.

TABLE 5

| | Starting Oil | | | | | | | |
|---|---|---|---|---|---|---|---|---|
| | Toluene | | | | Xylene for Isomerization | | | |
| Composition of Reaction Products (wt %): | Catalyst | | | | | | | |
| | E | F | e | f | E | F | e | f |
| Decomposition products | 0.3 | 0.2 | 0.1 | 0.1 | 2.8 | 1.8 | 0.9 | 0.5 |
| Benzene | 2.8 | 2.5 | 2.6 | 2.2 | 1.2 | 0.8 | 5.7 | 4.6 |

TABLE 5-continued

| | Starting Oil | | | | | | | |
|---|---|---|---|---|---|---|---|---|
| | Toluene | | | | Xylene for Isomerization | | | |
| Composition of Reaction | Catalyst | | | | | | | |
| Products (wt %): | E | F | e | f | E | F | e | f |
| Toluene | 96.5 | 97.1 | 93.9 | 95.6 | 10.3 | 9.4 | 5.9 | 4.2 |
| Xylene | 0.4 | 0.2 | 3.0 | 2.8 | | | | |
| $C_{9+}$ Aromatic hydrocarbons | 0 | 0 | 0.4 | 0.3 | | | | |
| Ethylbenzene | | | | | 1.7 | 2.6 | 3.8 | 4.3 |
| p-Xylene | | | | | 19.8 | 20.2 | 16.2 | 16.6 |
| m-Xylene | | | | | 43.4 | 44.5 | 39.7 | 41.1 |
| o-Xylene | | | | | 19.6 | 19.9 | 17.8 | 19.5 |
| Total of xylene | | | | | 82.8 | 84.6 | 73.7 | 77.2 |
| $C_{9+}$ Aromatic hydrocarbons | | | | | 1.2 | 0.8 | 10.0 | 9.2 |

It can be seen that dealkylation reaction of ethylbenzene took place in the *presence of catalysts E or F whereas disproportionation reaction predominantly took place in the presence of catalysts e or f.

The characteristics of the rhodium-on-crystalline methallo-silicate catalyst according to the present invention over the conventional catalysts lie in that alkyl aromatic hydrocarbons having 7 to 10 carbon atoms can be used as starting oils and that it catalyzes dealkylation of such starting oils as a predominant reaction at low temperatures to produce not only benzene but also dimethylbenzene, etc. These characteristics are remarkable where crystalline aluminosilicate is used as a carrier. In particular, where crystalline aluminolanthanosilicate or crystalline aluminoferrosilicate is used, the reaction selectivity is further improved to increase the production ratio of more useful xylene.

Further, since the reaction proceeds at low temperatures, by-production of coke on the catalyst can be suppressed as compared with the conventional processes. As a result, the activity of the catalyst can be maintained for a prolonged period of time, leading to a reduction of production cost.

While the invention has been described in detail and with reference to specific examples thereof, it will be apparent to one skilled in the art that various changes and modifications can be made therein without departing from the spirit and scope thereof.

What is claimed is:

1. A process for hydrogenolytically dealkylating a hydrocarbon mixture which comprises dealkylating a hydrocarbon mixture mainly comprising alkyl aromatic hydrocarbons in the presence of hydrogen and a catalyst comprising 0.01–5 wt. % rhodium supported on a crystalline metallo-silicate pentasil zeolite carrier selected from the group consisting of, an aluminolanthanosilicate having a $SiO_2/Al_2O_3$ molar ratio of 50–1000 and a $SiO_2/La_2O_3$ molar ratio of 25 to 200, and an aluminoferrosilicate having a $SiO_2/Al_2O_3$ molar ratio of 50–1000 and a $SiO_2/Fe_2O_3$ molar ratio of 25 to 200, and wherein said dealkylating occurs at a reaction temperature from 300° to 450° C. and a reaction pressure from 5 to 50 $kg/cm^2$.

2. A process as claimed in claim 1, wherein said crystalline metallo-silicate pentasil zeolite is an aluminolanthanosilicate having a $SiO_2/La_2O_3$ molar ratio of 25 to 200.

3. A process as claimed in claim 1, wherein said crystalline metallo-silicate pentasil zeolite is an aluminoferrosilicate having a $SiO_2/Fe_2O_3$ molar ratio of 25 to 200.

4. A process as claimed in claim 1, wherein said alkyl aromatic hydrocarbons have an alkyl group containing 2 or more carbon atoms.

5. A process as claimed in claim 4, wherein said alkyl aromatic hydrocarbons contain 8 to 10 carbon atoms.

* * * * *